United States Patent [19]

Catarious et al.

[11] 3,969,079

[45] July 13, 1976

[54] DUAL CHANNEL PHOTO-OPTICAL CLOT DETECTION APPARATUS

[75] Inventors: Joseph Catarious, Harleysville, Pa.; Lyman Bethke, Trenton, N.J.; Richard Berman, Dresher, Pa.

[73] Assignee: Alphamedics Mfg. Corporation, Levittown, Pa.

[22] Filed: Jan. 8, 1975

[21] Appl. No.: 539,520

[52] U.S. Cl. ............................ 23/253 R; 23/230 B; 356/246; 356/39
[51] Int. Cl.² .................. G01N 33/16; G01N 21/24
[58] Field of Search .......... 23/230 R, 230 B, 253 R, 23/259, 292; 356/246, 39

[56] References Cited
UNITED STATES PATENTS

| | | | |
|---|---|---|---|
| 3,477,822 | 11/1969 | Hamilton | 23/253 R |
| 3,540,858 | 11/1970 | Röchte et al. | 23/253 X |
| 3,542,515 | 11/1970 | Scott | 23/230 R |
| 3,607,099 | 9/1971 | Scordato | 23/253 X |
| 3,622,279 | 11/1971 | Moran | 23/230 X |

Primary Examiner—R.E. Serwin
Attorney, Agent, or Firm—Lerner, David, Littenberg & Samuel

[57] ABSTRACT

A dual channel photo-optical clot detection system for the automatic determination of prothrombin times and activated partial thromboplastin times and other related coagulation tests. A circular tray is utilized, and is vacuum formed to provide cuvettes having uniform wall thicknesses in two circular paths and arranged with radially aligned cuvettes. A single light source is placed between the radial spaced cuvettes and thus provides a common source for two separate detectors measuring the clot time of samples in each cuvette. The automatic dual channel operation provides a fixed time for activated partial thromboplastin time test so that fixed incubation time for the tests can be obtained. Thus, the sample to be tested is maintained at a low temperature until only two stations before measurement, and, accordingly, fixed incubation periods can be determined and exact conditions can be maintained for accurate testing.

8 Claims, 7 Drawing Figures

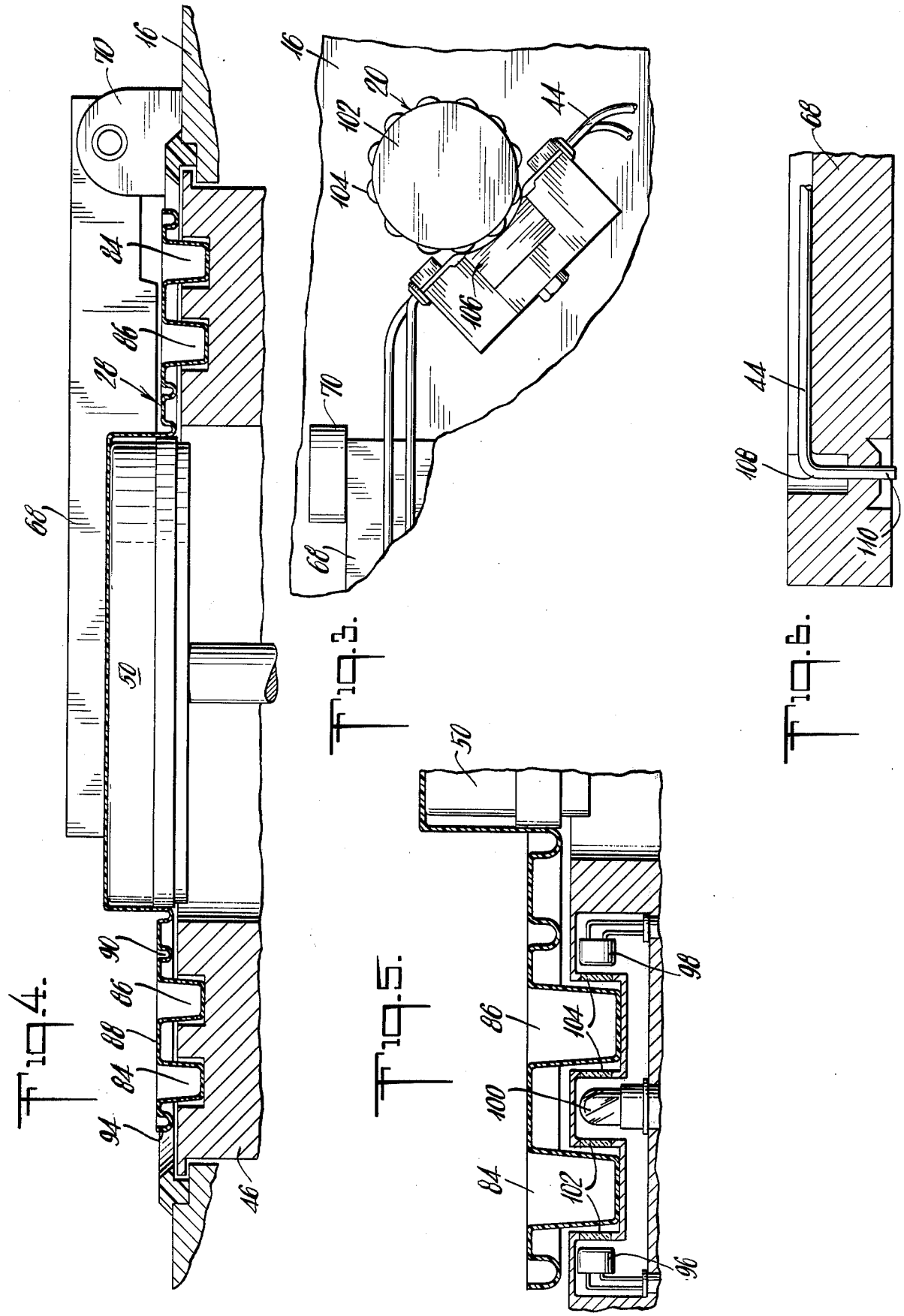

DUAL CHANNEL PHOTO-OPTICAL CLOT DETECTION APPARATUS

BACKGROUND OF THE INVENTION

Automated coagulation testing has been accomplished by apparatus developed in recent years. Thus, apparatus has been developed for testing plasma samples for prothrombin time, activated partial thromboplastin time, factor assays, and many other tests. Prior art devices have included means for pre-warming components in fluids and have utilized photoelectric systems for measuring coagulation time. In fact, such devices as the COAG-A-MATE single channel clot detection system sold by General Diagnostics Division of the Warner-Lambert Company has been very effective for such measurements. Devices for a similar purpose are manufactured by Medical Laboratory Automation, Inc. as the MLA Electra 620 and 600 Coagulation Timers. These devices have been described in U.S. Pat. Nos. 3,477,822 and 3,540,858. Additionally, many trays have been developed for testing samples photo-optically, which prior art devices are shown in U.S. Pat. Nos. 2,879,141; 3,038,340; 3,041,146; 3,368,872; 3,449,959; 3,469,438; 3,477,821; 3,477,822; 3,480,398; 3,480,399; 3,532,470; 3,540,858; 3,554,704; 3,544,705; 3,574,553; 3,594,129; 3,676,080; 3,690,833; 3,692,487; 3,692,488; 3,704,099; and 3,707,354.

None of the prior art devices were designed for the purposes of enabling a circular cuvette to measure, simultaneously, two samples utilizing a single source of light so that comparable measurements can be had of each sample. Further, it was difficult, if not impossible, to manufacture such a device without warpage of the cuvette in use, which warpage would prevent accurate measurements.

Further, prior art devices did not accurately insure uniform warm-up time for the sample and reagent under all test conditions.

SUMMARY OF THE INVENTION

The present invention is directed to a dual channel photo-optical clot detection system for the automatic determination of prothrombin times and activated partial thromboplastin times and other related coagulation tests. Whereas in the past, only single channel operation could be effected, the present invention is directed to a dual channel operation which can be effected within the same time period as prior art single channel systems. In such a system, twice as many plasma samples can be tested in the same period of time. Further, the same sample can be tested for both prothrombin time and activated partial thromboplastin time utilizing the same light source so as to prevent any error in the readings.

The cuvette utilized, avoids the necessity for separate test tubes and is rigid enough to prevent distortion due to warpage of the cuvette.

By utilizing the automatic clottage detection system of the present invention, there is provided a fixed time for the activated partial thromboplastin time test in that there is a fixed incubation time for these tests. Thus, the testing occurs through only three stations. Reagent is added at the particular indexing station in accordance with which test is being used. Reagent is added by means of a peristaltic pump which pumps reagent to the desired cuvette at a particular station.

Although this invention will be described with respect to its preferred embodiments, it should be understood that many variations and modifications will be obvious to those skilled in the art, and it is preferred, therefore, that the scope of the invention be limited, not by the specific disclosure herein, but only by the appended claims.

DETAILED DESCRIPTION OF THE DRAWINGS

FIG. 3 is a top plan view of the pump utilized with the system of FIG. 1.

FIG. 4 is a cross-sectional view taken along lines 4—4 of FIG. 1.

FIG. 5 is a cross-sectional view taken along lines 5—5 of FIG. 2.

FIG. 6 is a cross-sectional view taken along lines 6—6 of FIG. 2.

Figure 1:
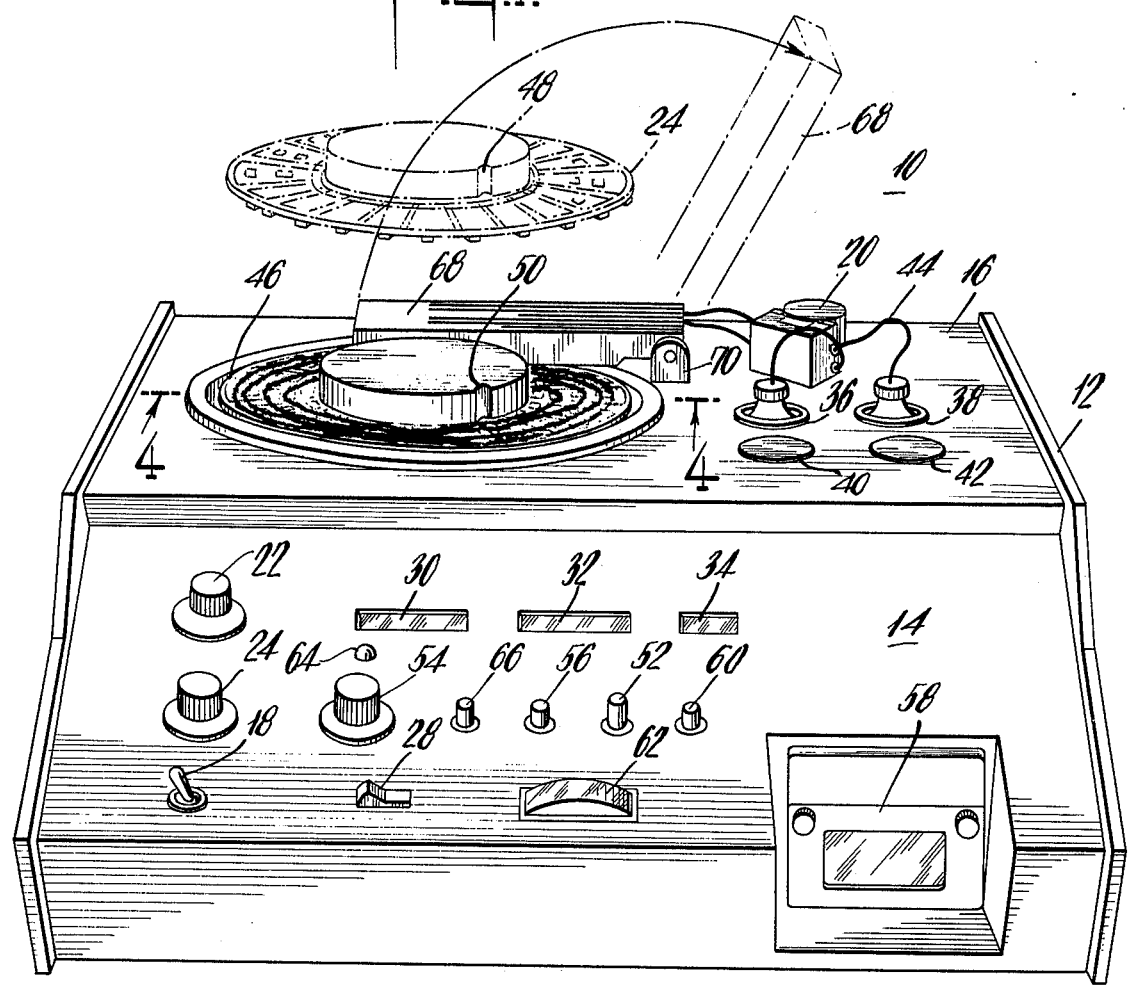
FIG. 1 is a front plan view of the photo-optical clot detection apparatus of the present invention.

In FIG. 1, there is shown the electro-optical measurement apparatus of the present invention generally designated by the numeral 10. The instrument 10 includes a housing 12 having a front panel 14 and a top panel 16. The front panel has a switch 18 thereon for setting the volume of reagent to be pumped by the peristaltic pump 20 when operating in the manual mode. For example, the switch 18 will, in the position shown, pump 0.2 milliliters for the prothrombin time measurement and in its second position pump 0.1 milliliters of reagent for the activated partial thromboplastin time measurement. The test mode is set by the switch 22 which determines whether the system operates for prothrombin time measurements, or activated partial thromboplastin time, or whether there will be simultaneous prothrombin time (PT) and activated partial thromboplastin time (APTT) in testing of similar samples.

A cycle time switch 24 is provided which sets the cycle time and utilizes the test mode to index the cuvette tray 26 into position for testing. Thus, with the cycle time switch on "demand" and the mode switch 22 on "PT," the apparatus will index on clot formation but not before 30 seconds. In the absence of clot formation, it will index at 150 seconds. If the cycle time switch is on demand, but the test mode switch 22 is on APTT, the test tray 26 will index on clot formation, but not before 110 seconds. In the absence of clot formation, it will index at 300 seconds. If clot formation exceeds 110 seconds, the activation times for the two subsequent samples will be extended.

The cycle time switch 24 also has a 50 second position. When used with the PT position of the mode switch, the instrument is used for PT testing and factor assays based on the PT system. The instrument allows approximately 2 minutes for incubation of the sample and indexes automatically every 50 seconds independent of clot formation.

When the cycle time switch 24 is in its 110 second position, it can be used in either the PT or the APTT mode. It is recommended for use with APTT reagents which require approximately 4 minutes for activation of sample and some factor assays based on the PT and APTT systems. It indexes automatically every 110 seconds independent of clot formation.

Similarly, if the cycle time switch is on the 150 second position, and the mode switch is set for APTT, the instrument is recommended for use with APTT reagents and most factor assays based on the APTT system which require approximately five minutes for activation of sample. The test tray 26 is indexed automatically every 150 seconds independent of clot formation.

Finally, the cycle time mode has two positions for 240 seconds or 300 seconds and is utilized with the test mode for APTT. Thus, it is for use in those tests requiring longer activation time on systems where extended clotting times are expected.

There is also provided an off/on switch 28 for turning on the power to the system. After the system has been turned on by the switch 28, the determination is made that the system is at operating temperature by viewing meter 62. Each of the displays 30 and 32 show, in time-seconds, digitally, the clotting time for specimens in the particular cavities to be measured. Display 34 indicates, digitally, the station at which the measurement is taking place. The position of the mode switch 22 determines the instrument time delay. Incubation time and delivery volume are selected by the cycle time switch 24 and the volume switch 18, respectively.

Reagents are placed in either the stir-cool or reagent storage wells 36, 38, 40 and 42, as required, and the reagent tubing assemblies 44 are primed with reagent.

Samples contained in the circular test tray 26 are placed on the incubation test plate 46. A keyway 48 is provided on the circular test tray 26 which cooperates with the keyway 50 on the incubation test plate so that the initial test station can be positioned by the table advance switch 52. The last station to be tested is selected with the final test switch 54. When the cycle start button 56 is pressed, the pump 20 automatically delivers reagent that initiates the clotting reaction, and simultaneously the electronic clock is activated. After a delay time of 8 seconds for the PT test and 20 seconds for the APTT test, the electro-optical sensor is activated. This delay is required to prevent premature end points caused by turbulence due to reagent delivery.

Clot formation is detected by a rate of change in absorbence that exceeds a predetermined level for defined periods of time. The results of the test are also printed out on the recorder 58. The pump can be primed by means of switch 60 and the temperture is read by suitable meter 62. An indicator light 64 indicates the end of a test procedure. A suitable button 66 is provided for termination of the test cycle.

The circular test tray 26 is disposable and has 24 positions to thus provide 48 cavities in which plasma samples may be incubated and tested. The cycle start button 56 may be used for initiating automatic test cycling and the cycle time switch 24 selects the indexing time between tests. The reagent dispensing pump 20 is a peristaltic pump of standard design which delivers reagent from the stir-cool wells 36 and 38 to a reagent incubation arm 68. The reagent incubation arm 68 is pivotal on a support 70. The reagent incubation arm warms reagents to a reaction temperature prior to delivery using a dry heat incubation system.

The print module 58 is a paper tape impact printer which records station number, test mode (P=PT and A=APTT), and end point time in seconds and tenths of a second. The results are presented in the format:

```
             1 3 P 0 1 3. 6————————Inner Channel Result
             1 3 P 0 1 3. 9————————Outer Channel Result
STATION—————┘ └————————————————MODE
             1 2 P 0 1 5. 0
             1 2 P 0 1 5. 0
             1 1 P 0 2 1. 0
             1 1 P 0 2 1. 0
             1 0 P 0 1 0. 9
             1 0 P 0 1 0. 9
```

Figure 2:
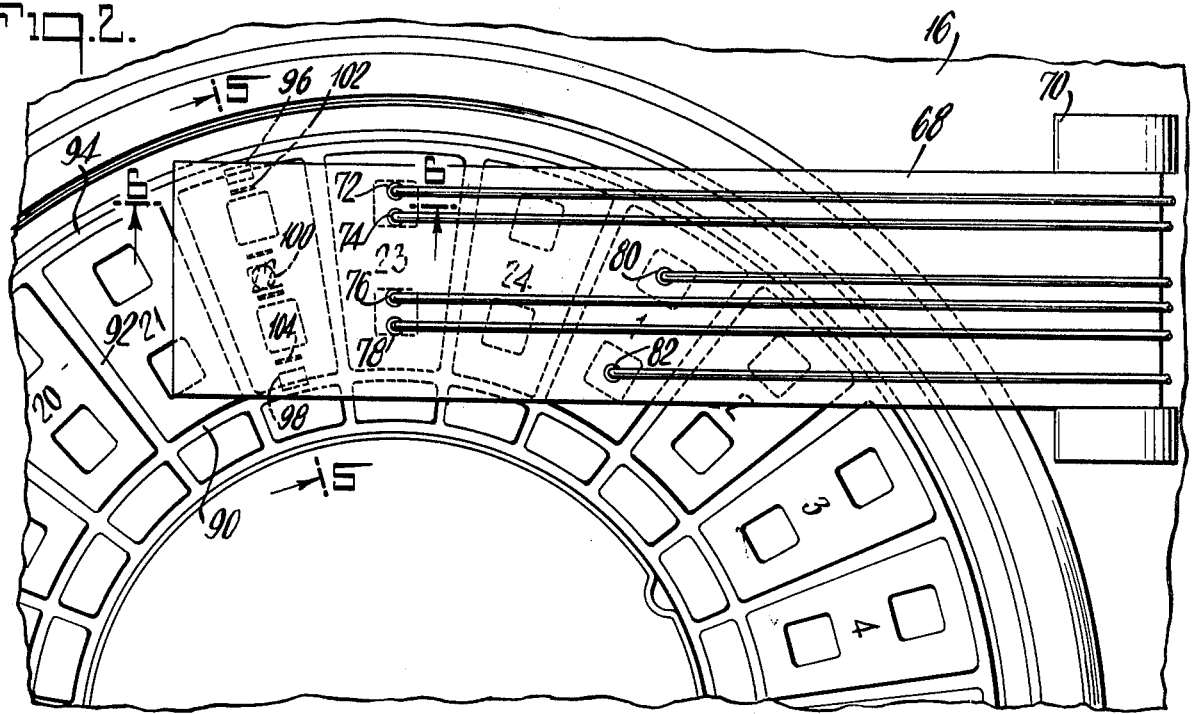
FIG. 2 is a top plan view of the apparatus of FIG. 1 with the pump in position.

As shown in FIG. 2, the reagent incubation arm 68 delivers reagent at points 72, 74, 76 and 78 at a first pair of radial test cavities. Reagent incubation arm 68 is also capable of delivering reagent at points 80 and 82 in a separate cavity spaced from the first-mentioned pair of cavities by one station. The delivery of reagents at points 80 and 82 are for the APTT test procedure. The delivery of reagent to points 72, 74, 76 or 78 for use with the PT test procedure. To test for PT, the reagent is prepared by reconstituting thromboplastin according to a manufacturer's instructions. If necessary, a small stirring bar may be utilized for mixing to maintain suspension. The vials of reagent are placed in the stir-cool wells 36, 38 and are capped with three-hole rubber stoppers. The tubing assembly 44 is placed into the reagent vials making sure the pick-up tip touches the bottom of the vial. The reagent tubing assembly is primed with reagent by pressing the prime button 60. Excess reagent thus primed is delivered into a piece of lint-free tissue held one-half inch from the delivery tip of the reagent incubation arm. The tubing is inspected for bubbles and repriming is completed if bubbles are present. To test, 0.1 milliliters of plasma is transferred to the inner and outer cuvettes of a test station in a circular test tray 26. Specimens are not placed in cuvettes at stations 23 and 24. These cuvettes are used to collect excess reagent dispensed during priming in the initial incubation period. As shown in FIG. 2, stations 2 through 21 are maintained at a low temperature. At stations associated with trays 23 and 24, the temperature is raised to 37°C. The circular test tray 26 is placed on the incubation test plate with key 48 matching key 50 and the reagent incubation arm 68 is lowered into place. The final test switch 54 is set for the last station to be tested. Then, the cycle start button 56 is pressed to initiate an automatic test cycle. When a visual time-second display stops, the test is completed and the PT is indicated in seconds and tenths of seconds. The display will remain unchanged until the results are printed and a circular test tray advances to the next position. The instrument operates automatically until a final test is completed. At each indexing, preheated reagent is pumped at 37°C with 0.2 milliliters of reagent being added to 0.1 milliliters of plasma. For the activated partial thromboplastin time test, Platelin Process Activator is added to the plasma at the points 80 or 82 and, thence, after predetermined incubation time, i.e., 5 minutes or 4 minutes, depending upon the setting, 0.1 milliliters of 0.025 M calcium chloride is added to the mixture through points 72, 74, 76 or 78 and reading is taken. It can thus be seen that since the time period is nearly two stations, there is an accurate setting for the heating of the mixtures and this setting is repeatable for each indexing of the circular test tray.

As can be seen from FIG. 4, the circular test tray 28 has outer cuvettes 84 and inner cuvettes 86 formed out of the plane of the upper surface 88 of the test tray 28. The test tray 28 is manufactured of a polyvinyl chloride, cellulose acetate, cellulose propionate or polypropionate transparent thermoforming material. It is imperative that the cuvettes 84 and 86 have a uniform wall thickness in order to get uniform optical transparency for measurement purposes. Ribs 90, 92 and 94 perform a dual function. The radial and circular ribs, cooperate to provide a radial construction which prevents warpage in use. Additionally, the radial ribs act as gathering points for plastic material resulting from the vacuum forming of the cuvette tray and further prevent bridging of the cuvettes in the area of the photosensing. The circular test tray can be formed by vacuum forming, pressure forming, mechanical pressure forming, air pressure forming and free forming by vacuum or air pressure. It cannot be manufactured by injection molding because of the need for thin transparent walls 0.007 inches in thickness. It is impossible for injection molding to achieve this type of uniform wall thickness with such small dimensions. The use of the ribs 90, 92 and 94, i.e., radial ribs spacing the pairs of cuvettes and joined by circular ribbing, provide the treble function of acting as gathering points for the plastic found in the forming process, giving strength and rigidity to the circular test tray, and further preventing bridging so as to enable accurate photosensing to be achieved.

In FIG. 5, the photosensing is shown. Thus, at the sensing station, photo cells 96 and 98 are positioned on opposite sides of the incubation test plate cavities to receive light from lamp 100 positioned to transmit light in opposite directions through outer cuvettes 84 and inner cuvettes 86. Suitable filters 102 and 104 are positioned in the recesses of the incubation test plate so that uniform light is received on photodetectors 96 and 98. The detectors allow for dual channel operation and thus a sample can be tested under the exact same conditions for different properties. This is especially useful when operating on the demand cycle as it insures standard incubation times. Further, the dual channel operation doubles the speed of testing for the operator and by utilizing the same light source, conditions can be set to assure uniform measurement after initial calibration of the detectors 96 and 98.

As shown in FIG. 3, the peristaltic pump 20 is of a standard construction comprising a rotor 102 having spaced rollers 104 around the surface thereof, which rollers compress four separate tubes in the tube assembly 44 against shoe 106 to pump, in a standard manner, liquid to the reagent incubation arm 68. As shown in FIG. 6, the reagent incubation arm 68 has a tube 44 resting in a slot therein which then has a delivery tip 108 extending vertically downwardly into a suitable hole in the bottom of the reagent arm 68 to form a nozzle 110. The delivery tip is set at 1/16 to 1/32 inch below the nozzle so that it feeds reagent directly into the appropriate cuvette.

Figure 7:
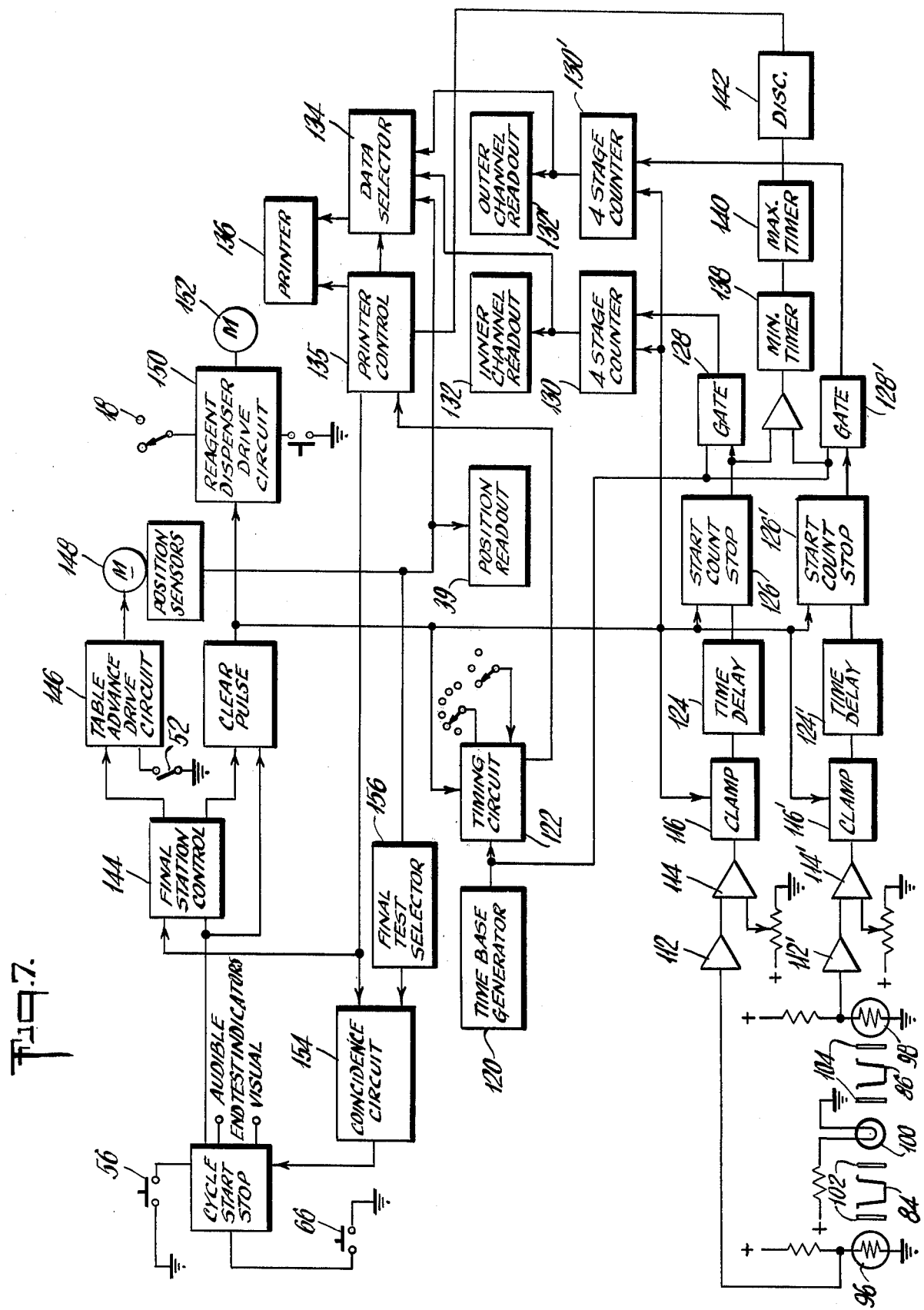
FIG. 7 is a schematic drawing of the control circuitry for the apparatus of the present invention.

In FIG. 7, there is shown the electronic circuitry in schematic form, for the apparatus of the present invention. In FIG. 7, there is shown the light source 100 supplied from a suitable DC supply utilized in supplying light for measuring the density of the fluid in cuvettes 84 and 86 at a given station. The filters 102 and 104 separate the cuvettes 84 from the light source and the photodetectors 96 and 98, respectively. The photodetectors 96 and 98 are operative to transmit signals through the amplifiers 112 and 112' and thence comparator circuits 114 and 114'. Here, the comparator circuits 114 and 114' will not transmit a signal unless the detectors 96 and 98 have submitted a signal which indicates a density over a given value. The output of the comparators 114 and 114' are prevented from continuing to be transmitted by clamping circuits 116 and 116' which, for the APTT test is set for 20 seconds, or the PT test is set for 8 seconds by the time base generator 120 and its associated timing circuit 122. An 8 or 20 second delay is to avoid errors due to turbulence during initial mixing of reagent with plasma. Thereafter, the clamp circuit feeds a time delay circuit 124 or 124' which is merely used to correct the answer to fit the expected result with manual readings. Thence, the output of the time delay circuits 124 and 124' are fed through counting circuits 126 and 126' and gates 128 and 128' to counters 130 and 130'. These signals are supplied to the inner channel readout 132 and the outer channel readout 132', respectively. Also, these signals are supplied to a data selector 134, which also feeds printer 136. The counters 126 and 126' also feed the minimum timers 138 and maximum timer 140 through a discriminator 142 to the printer control 144 so that only usable data is supplied to the printer 136. The cycle start switch 56 is operative to start the operation by transmitting a signal to the final station control 144 and thence to the table advance drive circuit 146 which controls the motor 148 which rotates the circular test tray. At the same time, the final station is also receiving signals from the reagent dispenser drive circuit 150 controlled by switch 18 and driving motor 152 driving peristaltic pump 20. When signals from the printer control 144 indicate that a reading has been obtained, a signal is sent to the coincidence circuit 154 in cooperation with the final test selector signal 156 for indicating another signal should be sent to the table advance drive circuit to continue the operation. Button 66 can be used to stop or halt the test cycle.

Although this invention has been described with respect to its preferred embodiments, it should be understood that many variations and modifications will now be obvious to those skilled in the art, and it is preferred, therefore, that the scope of the invention be limited, not by the specific disclosure herein, but only by the appended claims.

We claim:
1. A photo-optical clot detection apparatus comprising:
   a plurality of plasma sampling stations,
   means for indexing said plasma sampling stations into a readout position in between a radiant source and a radiation detector for measuring sample density,
   reagent feeding means for automatically feeding reagent to said plasma sampling stations at said readout position and a predetermined number of positions before said readout position,
   heating means for heating said plasma sampling station only between said readout position and said predetermined number of positions before said readout position, and
   timing means for controlling said indexing means to cause a sample of plasma to remain in said readout position and in the predetermined number of positions immediately prior thereto for only a set period of time.

2. The photo-optical clot detection apparatus of claim 1, wherein said predetermined number of positions is two.

3. A photo-optical clot detection apparatus comprising:
   a plurality of plasma sampling stations, means for indexing said plasma sampling stations into a readout position inbetween a radiant source and a radiation detector for measuring sample density, reagent feeding means for automatically feeding reagent to said plasma sampling stations at said readout position and a predetermined number of positions before said readout position, heating means for heating said plasma sampling station only between said readout position and said predetermined number of positions before said readout position, timing means for controlling said indexing means to cause a sample of plasma to remain in said readout position and in the predetermined number of positions immediately prior thereto for only a set period of time, said plurality of plasma sampling stations being in the form of a circular test tray having an inner and outer circular array of cuvettes, said inner and outer circular array of cuvettes having individual cuvettes radially aligned, said radiant source being positioned whereby said circular arrays of cuvettes pass on opposite sides of said radiant source and said radiation detectors being positioned on the inside of said inner circular array and the outside of said outer circular array so as to receive radiation through said cuvettes from the same central radiant source.

4. The photo-optical clot detection apparatus of claim 1, wherein said circular tray is manufactured of a thermoforming transparent plastic material, each of said radially aligned cuvettes having a rib therebetween, said radial rib being joined by circular ribs extending around and outside of the outer circular array of cuvettes and inside of the inner circular array of cuvettes to rigidify said circular tray.

5. The photo-optical clot detection apparatus of claim 4, wherein said cuvettes have thin transparent plastic walls, said thin transparent plastic walls being rigid, transparent and of uniform thickness.

6. A circular sample tray for a photo-optical clot detection apparatus comprising a flat tray formed of a transparent thermoforming plastic material, an inner circular array of cuvettes formed about the center of the tray and extending out of the plane thereof, an outer circular array of cuvettes formed concentric with said inner array of cuvettes and radially aligned therewith, and extending out of the plane of said tray, radial ribs extending between radially aligned inner and outer cuvettes, said radial ribs being joined by an outer circular rib extending around and of a greater diameter than the outer circular array of cuvettes, said radial ribs further being joined at their innermost end by an inner circular rib having a smaller diameter than the diameter of said inner circular array of cuvettes.

7. The circular tray for a photo-optical clot detection apparatus of claim 6, wherein said cuvettes have rigid, transparent wall surfaces of uniform thickness.

8. The photo-optical clot detection apparatus of claim 3 wherein said circular tray is manufactured of a thermo-forming plastic material, and indexing means to position said circular tray accurately with respect to said sampling stations formed on said tray cooperate with said means for indexing said plastic sampling stations.

* * * * *